United States Patent [19]

Miszczak

[11] Patent Number: 5,119,681

[45] Date of Patent: Jun. 9, 1992

[54] TEST FIXTURE

[75] Inventor: Frank Miszczak, Frankfort, Ill.

[73] Assignee: Fel-Pro Incorporated, Skokie, Ill.

[21] Appl. No.: 480,753

[22] Filed: Feb. 15, 1990

[51] Int. Cl.[5] .......................... G01N 3/08; G01M 3/00
[52] U.S. Cl. .............................. 73/788; 73/831; 73/37
[58] Field of Search ............... 73/788, 794, 795, 796, 73/808, 843, 816, 817, 818, 819, 821, 825, 826, 822

[56] References Cited

U.S. PATENT DOCUMENTS

| 2,346,281 | 4/1944 | Templin | 73/825 |
| 3,643,496 | 2/1972 | Zajic | 73/816 |
| 4,627,293 | 12/1986 | Bechtel | 73/826 |
| 4,850,231 | 7/1989 | Ralfs et al. | 73/818 |

OTHER PUBLICATIONS

Document A (includes Photographs 1, 2 and 3).
Document B entitled ASTM Designation: F 37-87 (Standard Test Methods for Sealability of Gasket Materials[1]).

Primary Examiner—Hezron E. Williams
Attorney, Agent, or Firm—Dressler, Goldsmith, Shore, Sutker & Milnamow, Ltd.

[57] ABSTRACT

A test fixture for testing a specimen under compressive or tensile load under close, reproducible tolerances and conditions. Confronting platens having surfaces which act against the specimen are provided with an in-line wedge assembly which drives the platens to load the specimen. The platens and wedge assembly are positioned between the top and base of a frame assembly. The top and base are connected by side plate members which are tensioned when the wedge assembly is operated to load the specimen via the platens. The test fixture also has a load cell in line with the platens and which is acted against by the platens to continuously sense the load applied to the specimen.

2 Claims, 5 Drawing Sheets

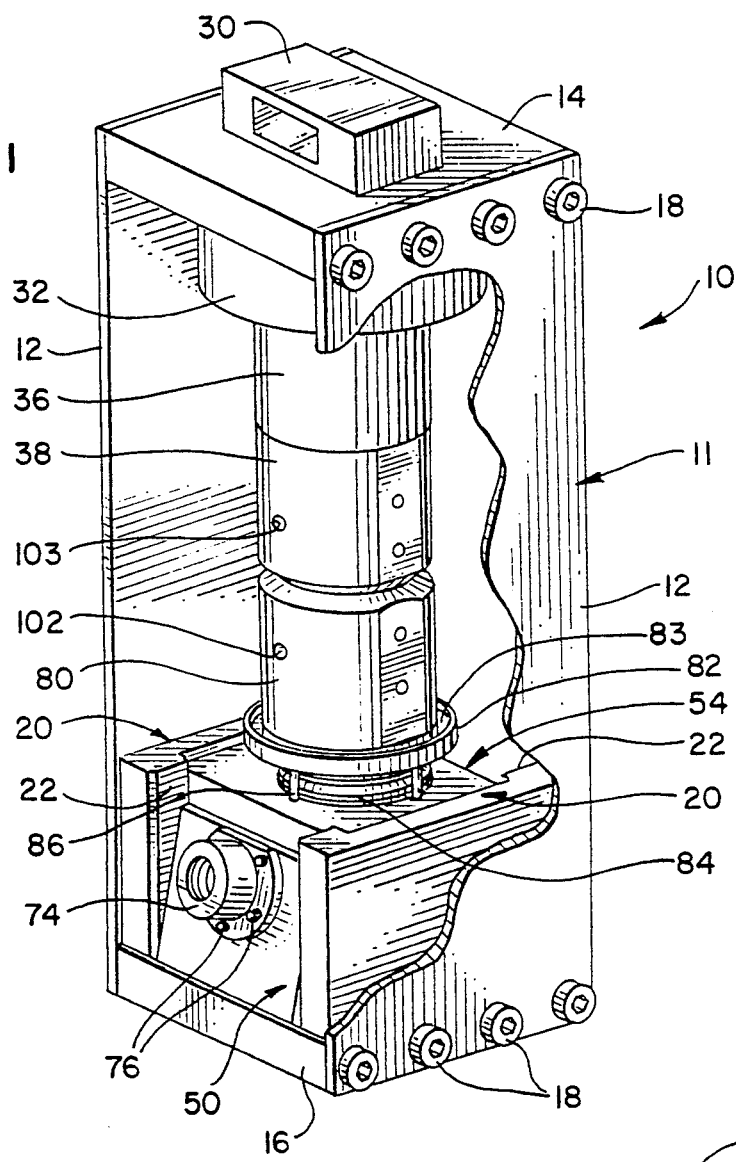
FIG. 1
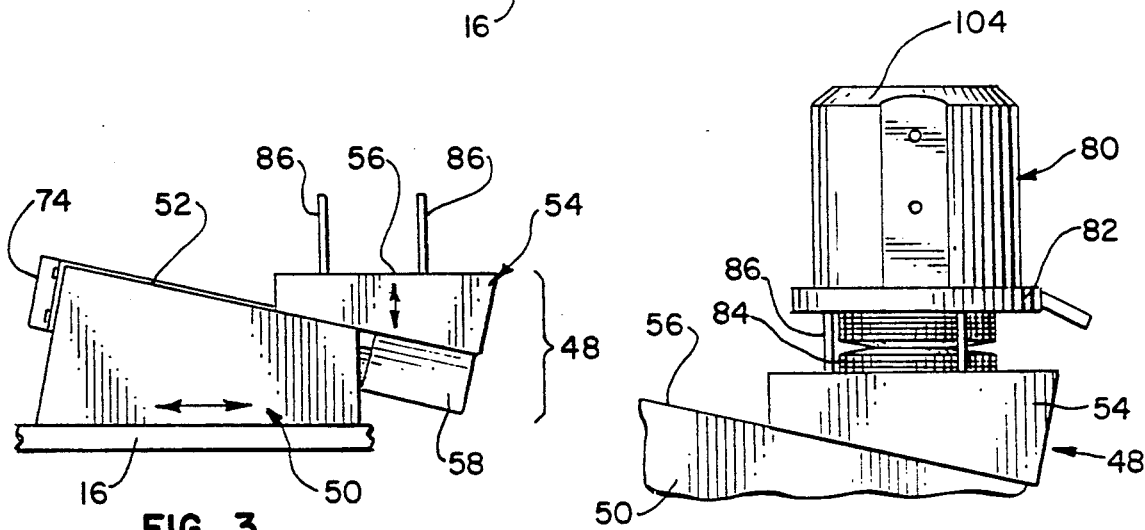
FIG. 3
FIG. 4

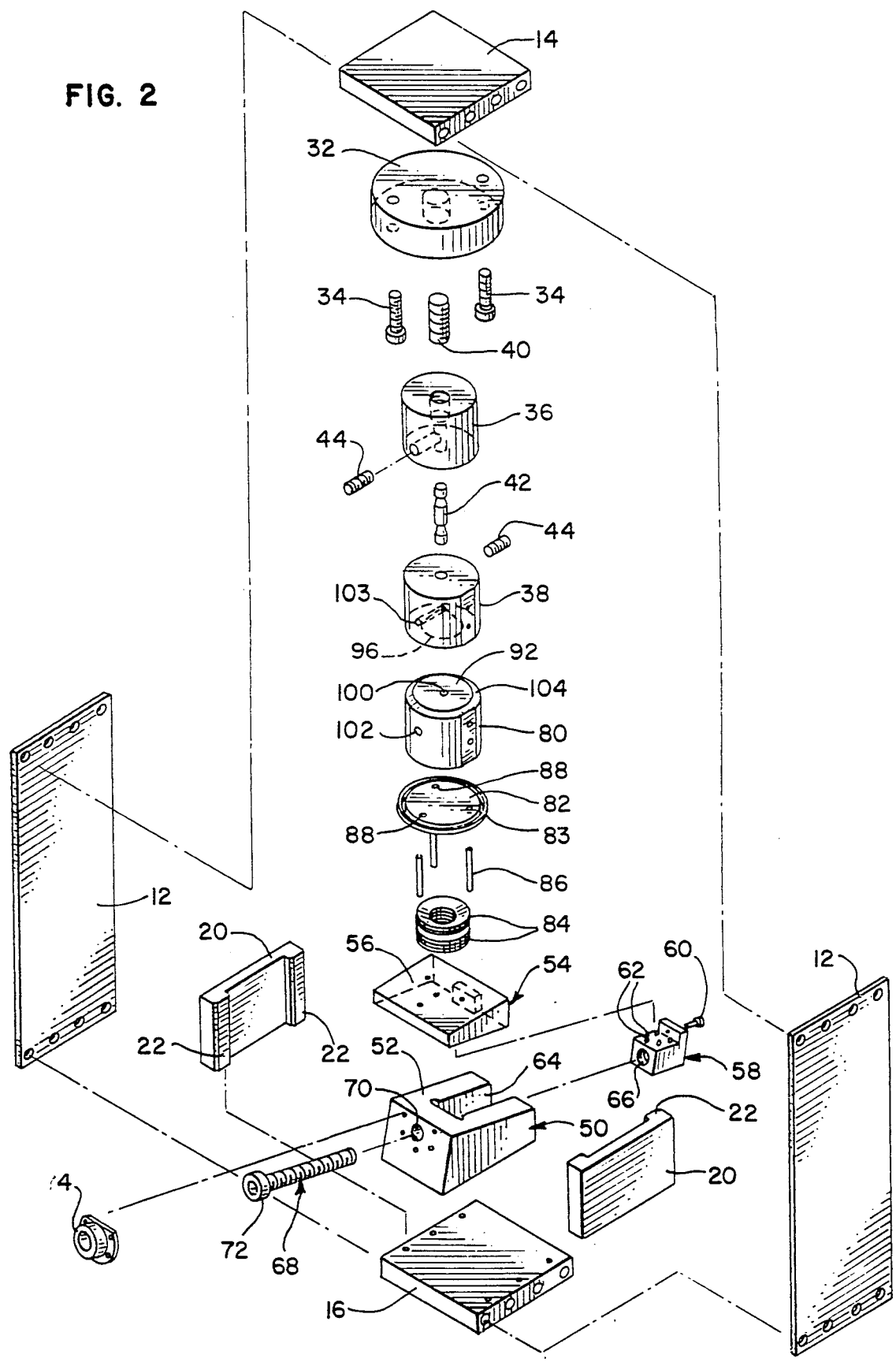

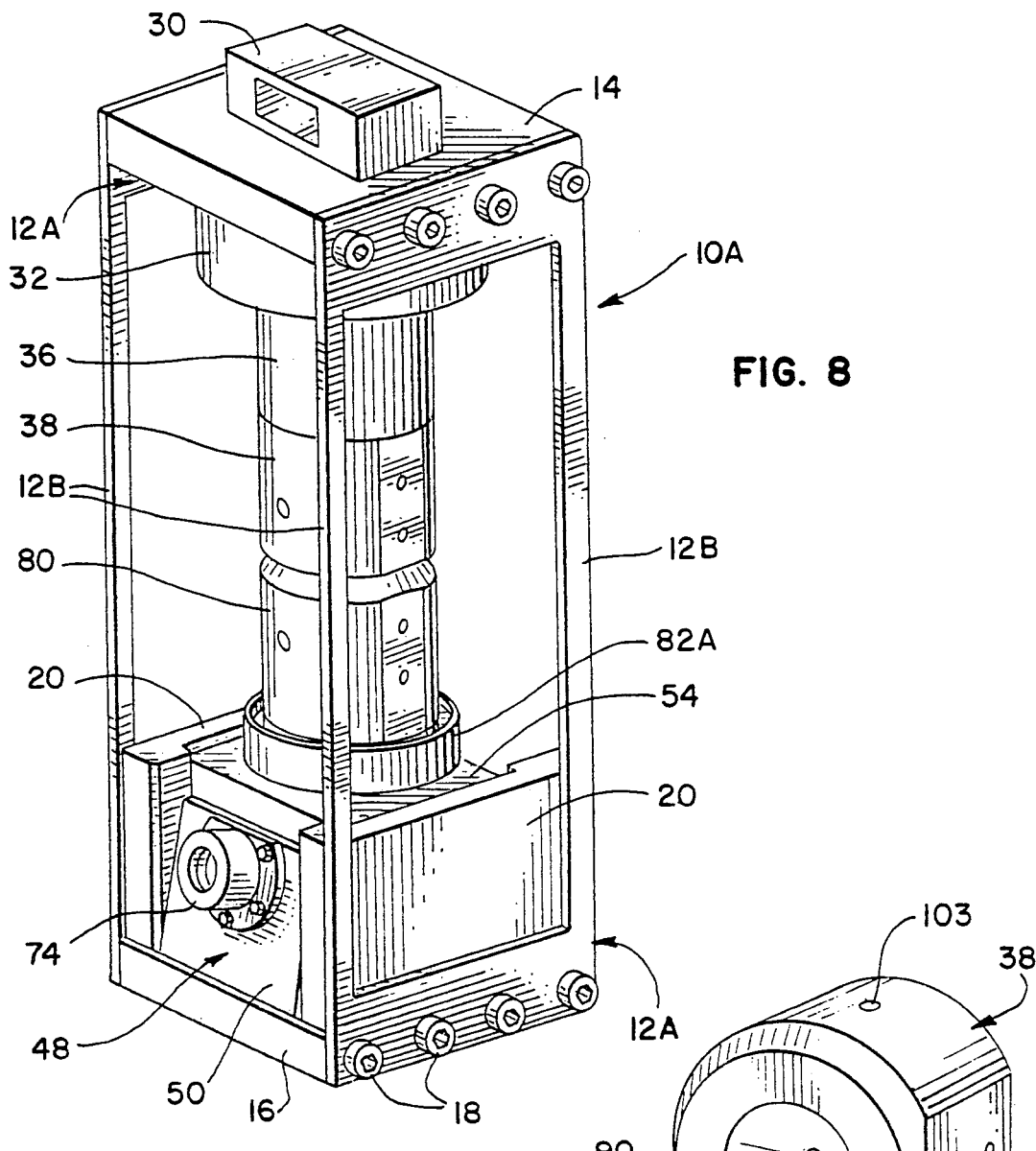
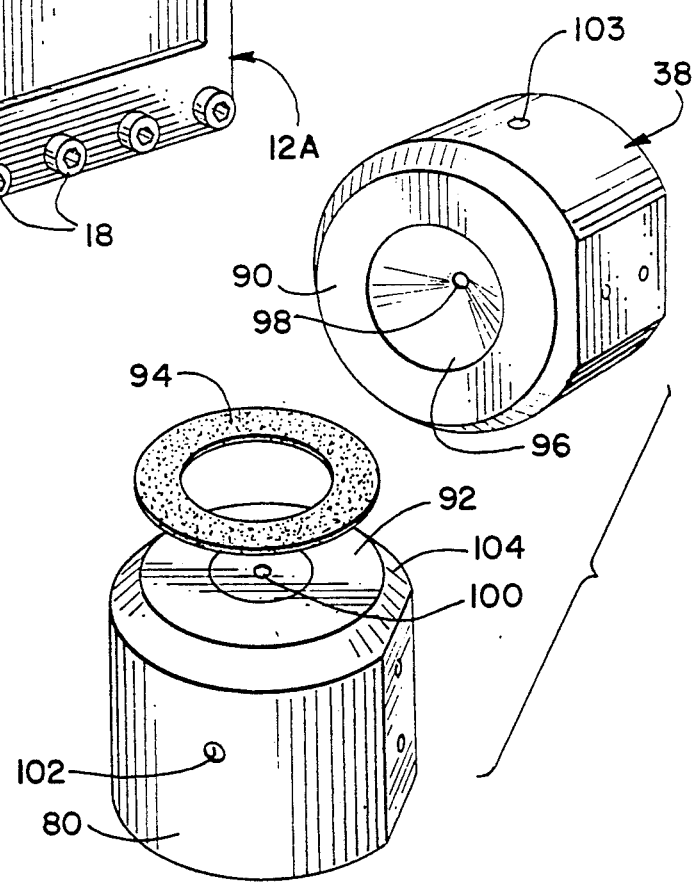
FIG. 8
FIG. 5

TEST FIXTURE

BACKGROUND OF THE INVENTION

It has been known to be desirable for some years now to provide test methods and devices for evaluating properties of materials and parts, such as, for example the sealing properties of sheet and formed gasket materials. Standard test methods for fluids are described in ASTM F37-87, both for liquids and gases.

Test methods and apparatus currently in use for those purposes have a number of limitations. For example, they typically require constant attendance and do not lend themselves to automatic, unattended operation. Further, they do not typically provide accurate, continuous load readout information. Further, they do not provide simulated adjustability for anticipated operating conditions, such as with regard to anticipated bolt stretching, thereby to accommodate to sealing material stress relaxation, bolt stiffness, etc.

Thus, it is clear that improved devices and test fixtures for carrying out tests such as of the sealing properties of gasket materials are desirable. It is also clear that improved test fixtures for testing other materials and parts are also desirable.

SUMMARY OF THE INVENTION

In accordance with the present invention, a test fixture for testing a specimen under load under reproducible tolerances and conditions is provided. The test fixture comprises a frame assembly having a top and a base which are connected as by side plate members to be loaded, and upper and lower platens having platen surfaces disposed to act oppositely against a specimen to be tested under load. The upper and lower platens are positioned within the frame assembly between the top and base. A wedge assembly comprising a pair of confronting wedge members in slidable bearing engagement with each other is also provided, the wedge assembly being positioned within the frame assembly between the top and the base, with one of the platens being positioned on one of the wedge members. Means are also provided for sliding one of the wedge members of, and relative to, the other wedge member to move the one of the platens toward and away from the other of the platens to load the specimen and to load the frame assembly in tension. Desirably the wedge assembly comprises a threaded member for moving a lower wedge member to and for to move an upper wedge member up and down. The upper wedge member is preferably adapted to move up and down only, and the lower wedge member is adapted to move the upper wedge member up and down. The frame assembly may mount guide means for the upper wedge member to guide the upper wedge member up and down as the lower wedge member is moved to and fro.

The platen may define surfaces which are positioned to act on a specimen in tension or the platens may define surfaces which are positioned to act on a specimen in compression. In one form of the invention, the platens comprise interdigitated members.

One form of a test fixture of the present invention, as used for testing the fluid sealability of a specimen of gasket material, comprises a frame assembly, upper and lower platens between which a specimen of gasketing material is adapted to be clamped, the platens being mounted on the frame assembly a movement toward and away from each other, a wedge assembly comprising a pair of confronting, upper and lower wedge members on slidable bearing engagement with each other and mounted on the frame assembly in line with the platens, and means for sliding one of the wedge members on, and relative to, the other wedge member to move one of the platens toward the other to clamp a specimen between confronting platen surfaces.

Preferably the frame assembly includes guide means for the upper wedge member for guiding the upper wedge member for movement up and down only relative to the lower wedge member and a threaded member is provided for moving the lower wedge member to and fro for moving the upper wedge member up and down.

The fluid sealability test fixture may also include means for simulating bolt stretch, such as compression spring means in line with the platens. Alternatively, the frame assembly side plates may be proportioned to provide for simulating bolt stretch by serving as tension spring means.

Desirably a load cell is mounted on the frame assemblies referred to, above and in line with the platens for continuously sensing the load applied to the specimen, and a read-out instrument associated with the load cell is provided to give a continuous readout of the load sensed by the load cell.

Further objects, features, and advantages of the present invention will become apparent from the following description and drawings.

BRIEF DESCRIPTION OF THE DRAWINGS

FIG. 1 is a perspective view, partially broken away, of a test fixture in accordance with the present invention which is adapted for testing the sealability of a material specimen;

FIG. 2 is an exploded perspective view of the test fixture of FIG. 1;

FIG. 3 is an illustrative side elevational view of a load adjustment wedge assembly of the test fixture of FIG. 1;

FIG. 4 is a fragmentary side elevational view of the load adjustment wedge assembly and surmounted bottom platen of the test fixture of FIG. 1;

FIG. 5 is an enlarged exploded perspective view of the platens of the test fixture of FIG. 1, showing a typical material specimen to be tested for material sealability;

FIG. 8 is a perspective view of a modified material sealability test fixture of the present invention;

DETAILED DESCRIPTION OF PRESENTLY PREFERRED EMBODIMENTS

Figure 6:
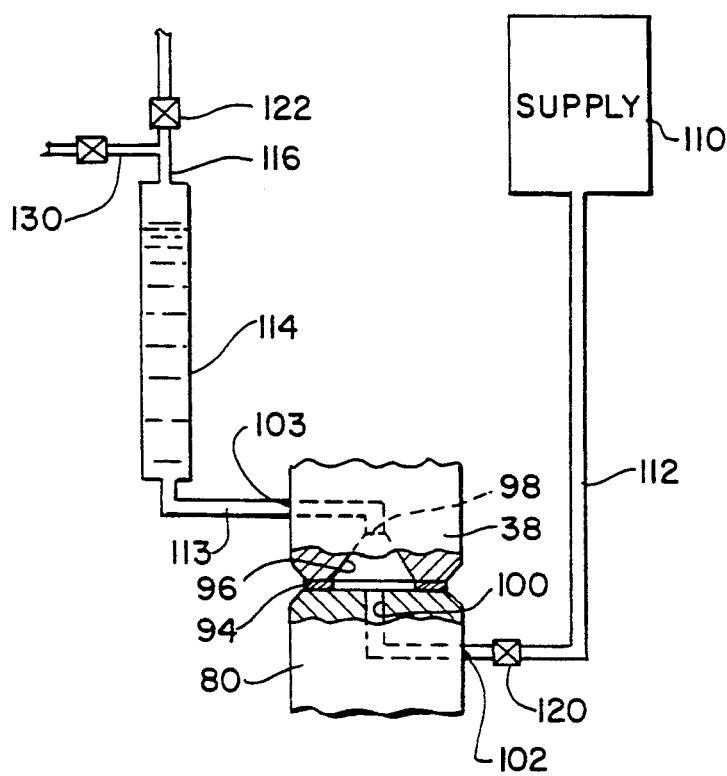
FIG. 6 is a schematic view of a liquid supply system for conducting a sealability test with the test fixture of FIG. 1.

A presently preferred embodiment of a test fixture of this invention is that shown in FIGS. 1 to 6, inclusive. Test fixture 10 is especially adapted for testing material sealability. As shown in FIGS. 1 to 6, test fixture 10 is adapted for testing a specimen under load and under close reproducible tolerances and conditions, and comprises a cage or frame assembly 11 having a top and a base, which are connected by metallic members (as of steel) to be loaded, such as side plates 12, a top plate 14 and a base or bottom plate 16. Plates 12, 14 and 16 are secured at the top and bottom respectively via screws 18 which pass through openings in the side plates into suitably threaded openings in the sides of the top and bottom plates. Guide means or bars 20 are positioned at each lower side of the frame assembly and are secured by screws (not shown) which pass through vertical openings in the bottom plate 16 into suitably threaded openings in the bottom edges of the guide bars. Each guide bar 20 defines forward and rear vertical portions or guides 22 to guide the top wedge for vertical movement, as will be described.

The top plate 14 mounts a readout instrument 30 and a load cell 32. Load cell 32 is secured against the lower surface of top plate 14, via mounting screws 34, which pass therethrough at appropriate locations. The lower surface of plate 14 defines suitably threaded openings to receive screws 34. A typical, suitable load cell is available from Sensotec, Inc. and is designated as Model No. 41. It continuously senses the load applied to it, hence to all parts of the test fixture between the top and bottom plates 14, 16.

An upper platen adaptor 36 and an upper or top platen 38 are also connected to the top plate 14. To that end a threaded connecting stud 40 is threaded into a complementary opening in the load cell 32 and into a similarly threaded opening at the top of the adaptor 36. A connecting pin 42 is seated in openings in adaptor 36 and in the top of top platen 38, and the adaptor 36 and platen 38 are retained in that juxtaposition via set screws 44 which engage the pin 42.

At the base of the test fixture 10 a wedge assembly 48 is provided. The wedge assembly comprises a pair of confronting wedge members in slidable bearing engagement with each other, and includes a lower wedge 50 which is seated for sliding movement on the upper surface of bottom plate 16. The upper wedge surface 52 is at an angle, such as at about 12 degrees to the horizontal, and is sufficiently expansive (see FIG. 2) to support and engage, without distortion, the lower wedge surface of a complementary upper wedge 54. When so supported, the upper surface 56 of the upper wedge 54 is preferably exactly horizontal when the test fixture 10 is disposed in a true upright position. The upper wedge 54 is proportioned, side to side and front to rear, to be snugly slidably received between guide bars 20, and in particular between the guides 22. As such, the upper wedge 54 is captured so that it may not move side-to-side or front to rear, but only up and down, as will be explained.

Upper wedge 54 is provided with a pull bar 58 secured at its rear, preferably by a threaded screw 60 and by a series of upstanding pins 62 which extend into mating openings in the lower surface of upper wedge 54. Pull bar 58 is proportioned to travel in a slot 64 in the lower wedge 54 as the lower wedge 50 is moved to and fro relative to the upper wedge 54.

To accomplish that, the pull bar 58 defines a clear through threaded opening 66 which is adapted to threadingly receiving a load adjustment screw 68. Screw 68 passes through a non-threaded opening 70 in the lower wedge 50 into threaded engagement with threaded pull bar opening 66. The head 72 of screw 68 bears against the front face of the lower wedge, and as screw 68 is rotated, it is adapted to draw the lower wedge forwardly relative to the captured upper wedge, thereby raising the upper surface 56 of the upper wedge. In use, the lower surface of the upper wedge 54 is fully supported on the lower wedge upper surface 52 (see FIG. 4), unlike the illustration of FIG. 3; thus, there is no possibility of canting of the upper wedge 54 in use.

As is clear, the platens and wedge assembly are in line with each other and are positioned within the frame assembly between the top and bottom plates.

A protective bearing collar 74 is positioned to cover the screw head 72, while leaving the adjustment opening accessible. The screw may be rotated by a suitably sized Allen wrench. Collar 74 is secured to the front face of the lower wedge by suitable mounting screws 76. To lower the upper surface of the wedge 54, the screw 68 is counter-rotated. Because the head 72 bears against the collar 74, the head 72 will drive the collar 74 outwardly, thereby carrying the associated lower wedge 50 outwardly (forwardly) to lower the upper wedge 54.

The upper surface 56 of the upper wedge 54 mounts the lower or bottom platen 80. The base of bottom platen 80 is positioned on an adapter 82 which serves as an overflow collector. The upper surface of adapter 82 is provided with a groove 83 to collect any overflow liquid and thus has an interior wall and a peripheral lip which serve as barriers to inward or outward flow of collected overflow liquid. Platen 80 (and adapter 82) are positioned and supported on a series of Belleville spring washers 84. Spring washers 84 are maintained in their centered positions relative to the platen 80 by guide pins 86 and upper wedge 56. Guide pins 86 are seated in openings in the upper surface of the upper wedge 54, extend vertically upwardly and pass, slidably, through openings 88 in adapter 82 (See FIG. 2) into openings in the bottom surface of bottom platen 80, thereby acting as guides for the bottom platen 80.

As seen in FIG. 5 upper platen 38 defines a platen or bearing surface 90 and lower platen 80 defines a platen or complementary bearing surface 92. These surfaces, which are disposed to confront each other and to act oppositely in compression against a specimen to be tested under load, in the present embodiment are carefully finished to be smooth and flat and parallel to each other when assembled in the test fixture. They are adapted to confront and engage a selected material specimen 94 in compression, and to be clamped together under selected load conditions to provide a basis for evaluating the sealability of selected specimens 94.

Platen 38 defines a conical cavity or opening 96 to hold a volume of fluid during testing. At the top of the opening 96 a fluid flow port 98 is provided. Similarly, platen 80 defines a fluid flow port 100. In each instance at least one of the fluid flow ports 98, 100 is in flow communication with a source of fluid, whether liquid or gas, under pressure, as through fittings secured as at openings 102, 103 in the sides of the platens. Should leakage of liquid through the material specimen occur during testing, it will flow outwardly, down the chambered or inclined surface 104 at the upper edge of platen 80, and down onto the adapter 82 where the associated upstanding wall and peripheral lip will retain it.

Referring now to FIG. 6, when the test fixture 10 is to be used under fluid pressure with a liquid, such as an engine coolant mixture of equal volumes of ethylene glycol and water, the mixture is caused to flow into the conical opening 96 from a supply vessel 110 through a supply line 112 into inlet opening 102, thence through port 100, conical opening 96, port 98, out outlet opening 103, into line 113, into a graduated tube 114 and out, if necessary, valved conduit 116. Flow is continued until all air or gas is purged from the lines and cavity 96 and the lines are completely filled with liquid. When that is accomplished, the valves 120 in line 112 and 122 in line 116 are closed and the liquid column in graduated tube 114 is pressurized, as at 50 pounds gauge pressure, via a suitably regulated air pressure line 130. Thus, during testing of a material specimen 94, the pressure in the conical cavity 96 may be closely maintained at a predetermined pressure level. A visual determination of the amount of liquid lost during a test cycle may be made by observing the level of the fluid column in graduated tube 114. The 50 pound test pressure is a typical pressure at which it is desirable to test exposed coolants in automotive coolant systems. Of course, other pressures for other environments may be used as well, and other systems for filling, purging and pressurizing the test fixture of this invention may be employed also.

The test fixture shown 10 may be used to test with gases, such as air, helium, nitrogen and others. In that case, it may be desirable to plug or block opening 103 and eliminate valve 120 altogether to avoid a possible leakage path. Then, the opening 102 is provided with a pressurized gas at a desired pressure which will serve, obviously, to provide pressurized gas in the conical cavity 96, and at the inner peripheral edge of the test specimen 94. The entry line 112 may be provided with a mass flow transducer which, after the system has been stabilized so that a test cycle may commence, measures the flow of gas, hence gas loss through the specimen, during the test cycle. Other measuring instruments for measuring the gas lost through the test specimen may be used as well.

In one form of the embodiment of FIGS. 1 to 6, the lower platen 80 has a flat specimen supporting surface having a 2.8 inch outside diameter dimension at the inclined surface edge, and an entry flowport diameter of 3/16 inch. The upper platen 38 has the same outside diameter and has a 45 degree cone which registers with the outlet flow port. Although other finishes, such as rougher finishes, may be used, preferably the sample mating surfaces may have a surface finish having a roughness average measurement of 6 to 8 Ra according to the DIN 4768 standard. Presently contemplated annular test specimens are designed to have a ½ inch leak path. Thus, the annular specimens have an outside diameter of 2.75 inches, an inside diameter of 1.75 inches and, as such, a surface area of 3.53 square inches.

It should be noted that the upper platen 38 may be rotated, if desired. Thus the set screws 44 may be loosened for that purpose, and retightened with the platen 38 in any desired circumferentially displaced position. Parallelism of the platen surfaces in various positions of relative rotation may be determined by using known load impression film techniques.

One of the features incorporated into the test fixture of FIGS. 1 to 6 is the capacity to simulate bolt stretch in various environments. It will be apparent that if the frame sides are sufficiently stiff, they will not stretch significantly under loading as the wedge assembly clamps the test specimen at desired loads. Under such circumstances, if the test specimen should relax under the stress imposed, the clamping load will reduce substantially, and leakage will be likely to occur for that reason alone. Load retention studies of the test fixture itself (metal to metal) have shown a maximum load loss of no more than 1.5% due to fixture system settling.

Because of that, the test fixture of the present invention has been designed to accommodate stress relaxation by introducing a simulation of the elastic bolt stretch which would occur in an actual application.

Figure 7:
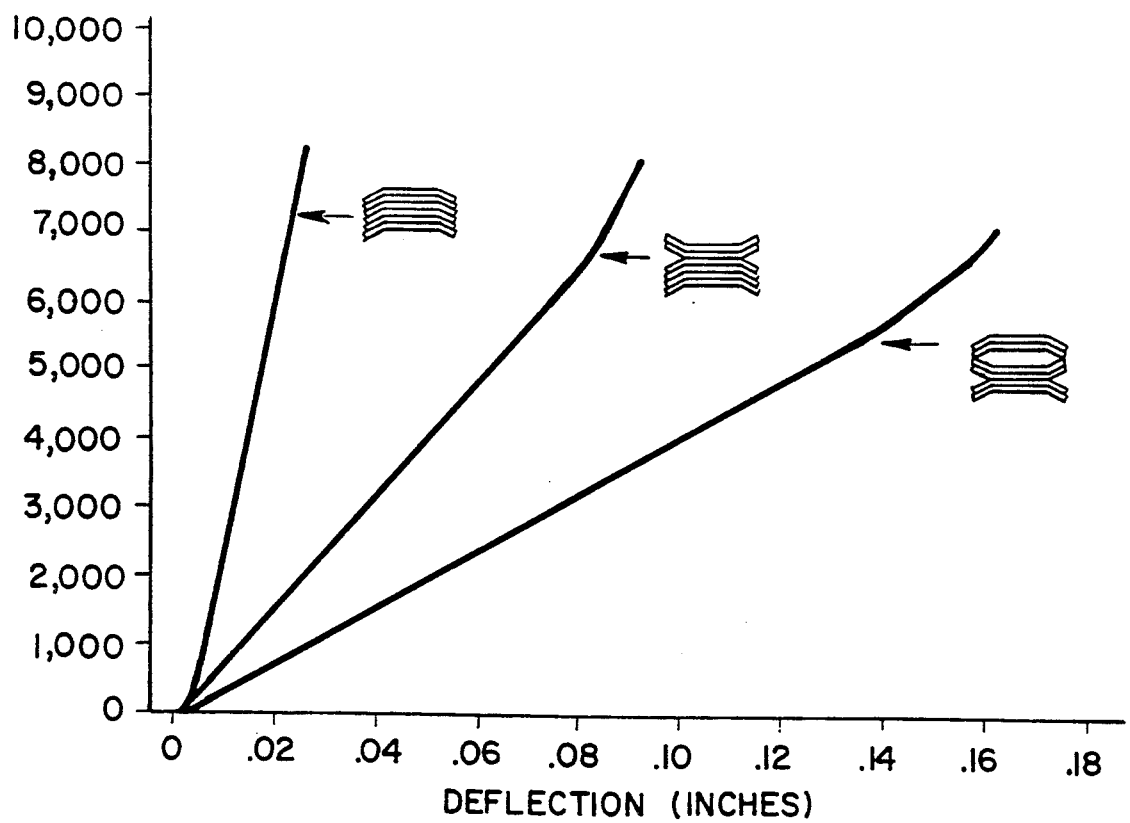
FIG. 7 is a graph showing typical varying load deflections which may be obtained by varying arrangements of Belleville springs as used with the test fixture of FIG. 1.

In the embodiment of FIGS. 1 to 6, this is provided by the Belleville spring washers 84 which are selected to fit the desired stiffness requirements for the material and conditions to be tested. Calibrated Belleville springs are available in various stiffness ranges. By using calibrated springs in selected multiple numbers, and in various arrays and arrangements, testing for different load conditions is made possible. This is illustrated by the graph, FIG. 7, which shows the same Belleville springs 84 arranged in three different arrays, producing deflections which are significantly different.

The embodiment of FIG. 8 is very much the same as that of FIGS. 1-6, with one notable exception. In the test fixture 10A of FIG. 8, the side plates 12A have been cut away and there are no Belleville springs or guide pins. However, dowel pins like guide pins 86, should be present to fix the bottom platen 80 relative to the upper wedge 54.

Thus, in FIG. 8 the identical steel side plates 12A consist primarily of four columns 12B (only 3 of which are seen). Columns 12B, unlike plates 12 of FIG. 1, may be allowed to stretch significantly under loading of the test fixture, but within the elastic limits of the metal. As such, stress relaxation of the test material is accommodated in the same manner as would clamping bolts under actual conditions. Thus, the columns 12B serve the same general function as do the Belleville springs in FIG. 1, but in a different manner.

The test fixtures shown in FIGS. 1-6 and 8 are specifically designed for acting in compression on a material specimen to be tested for sealability. It will be apparent that the test fixture as operated with the wedge assembly of the present invention may be used for operating on specimens and parts of other types, both in compression and in tension, and may therefore be used, for example, for testing bolts in tension.

To that end, as illustrated schematically by FIGS. 9 to 12, a test fixture 10C including a frame assembly 11 and wedge assembly 48 including wedges 50, 54 the same as those shown in FIGS. 1-5 may mount platens 38C, 80C which are respectively positioned, such as between the upper frame member 14 and the wedge assembly 48, in the same manner as platens 38, 80. Platens 38C and 80C may comprise U-shaped, interdigitated members or yokes, the upper platen 38C being secured suitably as by threaded members to the upper frame member, as via a load cell 32, and the other lower platen 80C being secured suitably to the upper wedge member 54 of the wedge assembly 48, as by dowel pins (not shown) passing downwardly through openings in platen 80C into the upper surface of wedge member 54. As such, the interdigitated platens 38C and 80C may be changed easily, thereby to permit the substitution of other platen members as may be desired.

Platen 38C may be formed from round steel bar stock and may define a cylindrical upper portion 302 with a pair of depending legs 304, the inner surfaces 306 of which may be flat and parallel. The legs 304 define opposing slots 308 which slidably receive a platen plate 310 which has ears 312 which slidably mate with slots 308, the upper surfaces of which ears bear against flange surfaces defined by the slots 308 (see FIGS. 10 and 11). Platen plate 310 may be removably secured by threaded fasteners or pins (not shown) to the platen 38C. Platen plate 310 defines a central opening 314 for a purpose to be described.

Figure 9:
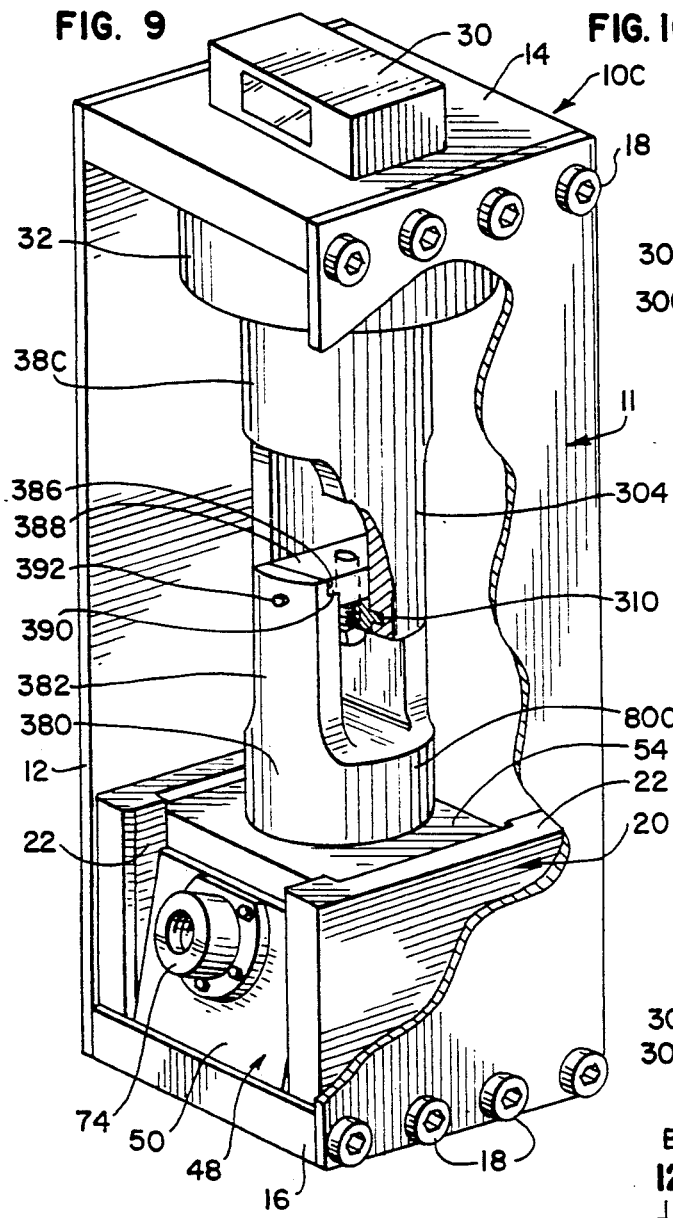
FIG. 9 is a perspective view, partially broken away, of a further test fixture in accordance with the present invention.

Platen 80C may also be machined from round steel bar stock and may define a cylindrical lower portion 380 with a pair of upstanding arms 382, the inner surfaces 384 of which are preferably flat and parallel. The arms define opposing grooves 386 which receive a platen plate 388 which has ears 390 which mate with grooves 386. The ears 390 bear against lower groove surfaces (see FIG. 9). Platen plate 388 may be removably secured to the platen 80C by threaded fasteners or pins 392 (FIG. 9). Platen plate 388 defines a central threaded opening 394 for a purpose to be described.

Although platens 38C and 80C have been described as being machined from round steel bar stock, they can be formed from square stock or may be otherwise fabricated from steel or other appropriate materials.

Figure 10:
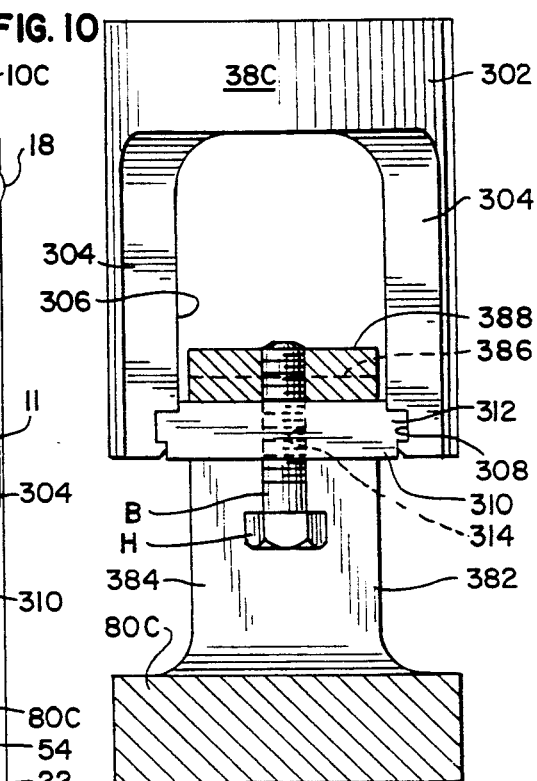
FIGS. 10 and 11 are enlarged side elevational views, partially in cross-section, of the platen assembly of FIG. 9 in first and second positions of movement of the wedge assembly.
Figure 11:
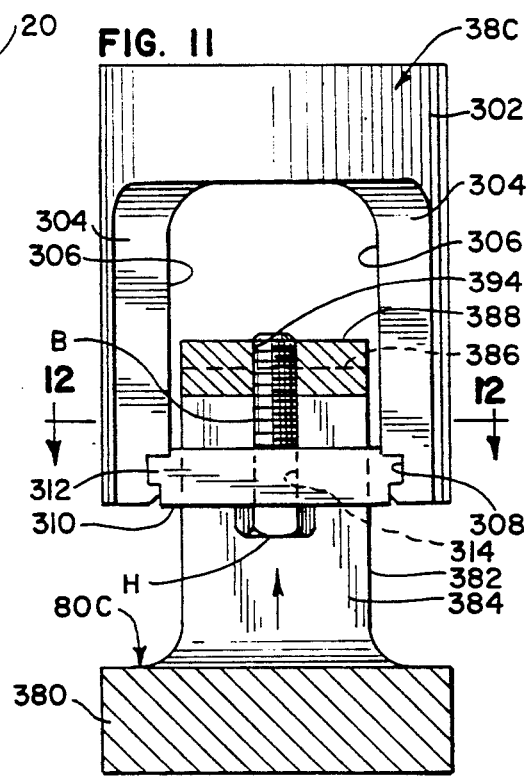
Figure 12:
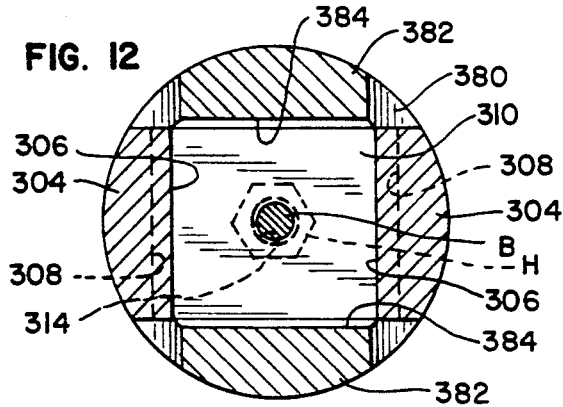
FIG. 12 is a view taken along line 12—12 of FIG. 11.

If a threaded bolt B is threadedly positioned in threaded opening 394 in the platen plates, with head H below platen 310, and the wedge assembly 48 is operated to move platen 80C upwardly from the position of FIG. 10 to that of FIG. 11, thereby to move the platen plates away from each other, the head H of bolt B will eventually contact platen 310. Further movement via the wedge assembly will then cause the bolt B to be tensioned. The test fixture may be used to test a variety of characteristics of the bolt B in tension. Of course the platen members 38C, and 80C are sufficiently stout and rigid, so that under compression they will remain as rigid as possible to avoid introducing stresses due to deformation of the platens.

Similarly, if a platen plate 388 is positioned below platen plate 310 using suitably sized and proportioned platens 38C and 80C, and the wedge assembly 48 is operated to move the upper wedge 54 upwardly, hence to move the platen plates towards each other, specimens positioned between platens 38C and 80C will be operated on in compression by the confronting platen surfaces.

Thus, the wedge assembly as used in the test fixtures is highly versatile and adaptable to the testing of a variety of materials, parts and objects, both in tension and compression, and to maintain good control over the loads applied as well as close maintenance over the parallelism of the confronting surfaces of the platens in a consistent manner, where, as is very frequently the case, that is important.

From the foregoing, it will be apparent to those skilled in the art that modifications departing from the specific embodiments described and illustrated may be made without departing from the spirit and scope of the present invention. Accordingly, there is no intention to be limited by the disclosure herein, except as may be made necessary by the claims appended hereto.

What is claimed is:

1. A test fixture for testing a specimen under load under close reproducible tolerances and conditions, comprising a frame assembly having a top and a base and connected by members to be loaded, upper and lower platens having platen surfaces disposed to act oppositely against a specimen to be tested under load, said upper and lower platens being positioned within said frame assembly between said top and base, a wedge assembly comprising a pair of confronting wedge members in slidable bearing engagement with each other, said wedge assembly being positioned within said frame assembly between said top and said base, with one of said platens being positioned on one of said wedge members, and means for sliding one of said wedge members on, and relative to, the other of said wedge members to move said one of said platens toward and away from the other of said platens to load said specimen in line with the direction of movement of said platen surfaces toward and away from each other and to load said frame assembly, and wherein said platens comprise interdigitated 2. A test fixture in accordance with claim 1, and wherein said platen surfaces engage a threaded fastener for tension in said threaded fastener as said wedge members move one of said platens away from the other.

* * * * *

UNITED STATES PATENT AND TRADEMARK OFFICE
CERTIFICATE OF CORRECTION

PATENT NO. : 5,119,681
DATED : June 9, 1992
INVENTOR(S) : Frank Miszczak

It is certified that error appears in the above-identified patent and that said Letters Patent is hereby corrected as shown below:

Column 1, line 44, "of" should be --on--;

Column 1, line 49, "for" should be --fro--;

Column 1, line 67, "a" should be --for--; and

Column 2, line 2, "on" should be --in--.

Column 8, line 43, insert --members.-- after "interdigitated"; and

Column 8, line 46, "tension in" should be --tensioning--.

Signed and Sealed this

Seventeenth Day of August, 1993

Attest:

BRUCE LEHMAN

*Attesting Officer*   *Commissioner of Patents and Trademarks*